United States Patent
Michihata

(10) Patent No.: US 10,134,105 B2
(45) Date of Patent: Nov. 20, 2018

(54) MEDICAL SIGNAL PROCESSING DEVICE AND MEDICAL OBSERVATION SYSTEM

(71) Applicant: Sony Olympus Medical Solutions Inc., Tokyo (JP)

(72) Inventor: Taihei Michihata, Kanagawa (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 34 days.

(21) Appl. No.: 15/384,879

(22) Filed: Dec. 20, 2016

(65) Prior Publication Data

US 2017/0206624 A1 Jul. 20, 2017

(30) Foreign Application Priority Data

Jan. 15, 2016 (JP) ................. 2016-006644

(51) Int. Cl.
*G06K 9/00* (2006.01)
*G06T 1/20* (2006.01)
*A61B 1/00* (2006.01)
*A61B 1/04* (2006.01)
*H04N 5/225* (2006.01)

(52) U.S. Cl.
CPC ............ *G06T 1/20* (2013.01); *A61B 1/00013* (2013.01); *A61B 1/00018* (2013.01); *A61B 1/00045* (2013.01); *A61B 1/00163* (2013.01); *A61B 1/04* (2013.01); *H04N 5/2256* (2013.01); *H04N 2005/2255* (2013.01)

(58) Field of Classification Search
None
See application file for complete search history.

(56) References Cited

U.S. PATENT DOCUMENTS

| | | | | | |
|---|---|---|---|---|---|
| 5,649,897 | A | * | 7/1997 | Nakamura | ......... A61B 1/00193 348/45 |
| 5,878,159 | A | * | 3/1999 | Taleblou | .................. G06T 1/00 348/65 |
| 6,016,211 | A | * | 1/2000 | Szymanski | .............. G02B 6/43 359/108 |

(Continued)

FOREIGN PATENT DOCUMENTS

| | | |
|---|---|---|
| JP | 2006-26134 | 2/2006 |
| JP | 2009-61032 | 3/2009 |

*Primary Examiner* — Shervin Nakhjavan
(74) *Attorney, Agent, or Firm* — Oblon, McClelland, Maier & Neustadt, L.L.P.

(57) ABSTRACT

A medical signal processing device processes an image signal received in accordance with a result of examining inside of a subject. The image signal includes pixel data groups that are data of respective pixels different from each other and received by the medical signal processing device in parallel. The medical signal processing device includes a distribution processing unit configured to generate distributed image signals by distributing the pixel data groups, and the distribution processing unit distributes the pixel data groups such that, among the pixel data groups, pieces of data at bit positions of most significant digits of the pixel data groups of pixels adjacent to each other are included in the respective distributed image signals different from each other. The distributed image signals are transmitted to an external medical control device through respective signal transmission paths.

7 Claims, 12 Drawing Sheets

(56) References Cited

U.S. PATENT DOCUMENTS

| | | | | |
|---|---|---|---|---|
| 6,697,101 | B1* | 2/2004 | Takahashi | H04N 7/183 348/65 |
| 7,292,275 | B2* | 11/2007 | Masuyama | G02B 21/365 348/221.1 |
| 7,587,261 | B2* | 9/2009 | Hopkins | G06T 1/0007 382/153 |
| 8,449,453 | B2* | 5/2013 | Fujimoto | A61B 1/00006 348/525 |
| 2007/0276198 | A1* | 11/2007 | Eli | A61B 1/04 600/300 |
| 2008/0123097 | A1* | 5/2008 | Muhammed | G01J 3/02 356/419 |
| 2011/0213203 | A1* | 9/2011 | Minai | A61B 1/00009 600/109 |
| 2012/0127292 | A1* | 5/2012 | Yamazaki | A61B 1/00009 348/68 |
| 2012/0308149 | A1* | 12/2012 | Sengoku | H04N 1/648 382/237 |
| 2013/0012777 | A1* | 1/2013 | Baum | A61B 1/00013 600/110 |
| 2013/0266078 | A1* | 10/2013 | Deligiannis | H04N 19/00533 375/240.25 |
| 2015/0022647 | A1* | 1/2015 | Takei | A61B 1/00186 348/70 |
| 2015/0305603 | A1* | 10/2015 | Gal | A61B 1/00167 600/103 |

\* cited by examiner

FIG.3A

| 0<br>(CA) | 1<br>(CB) | 2<br>(CC) | 3<br>(CD) | 4<br>(CE) | 5<br>(CF) | 6<br>(CG) | 7<br>(CH) | 8<br>(CI) | 9<br>(CJ) | 10<br>(CA) | ...... |
|---|---|---|---|---|---|---|---|---|---|---|---|
| △△<br>(CA) | △□<br>(CB) | △○<br>(CC) | △×<br>(CD) | □□<br>(CE) | □△<br>(CF) | □○<br>(CG) | □×<br>(CH) | ○△<br>(CI) | ○□<br>(CJ) | ○×<br>(CA) | ...... |

| | | | | | | | | | | |
|---|---|---|---|---|---|---|---|---|---|---|
| (a) FIRST CHANNEL CA | 0 (9) | 0 (8) | 0 (7) | 0 (6) | 0 (5) | 0 (4) | 0 (3) | 0 (2) | 0 (1) | 0 (0) |
| (b) SECOND CHANNEL CB | 1 (9) | 1 (8) | 1 (7) | 1 (6) | 1 (5) | 1 (4) | 1 (3) | 1 (2) | 1 (1) | 1 (0) |
| (c) THIRD CHANNEL CC | 2 (9) | 2 (8) | 2 (7) | 2 (6) | 2 (5) | 2 (4) | 2 (3) | 2 (2) | 2 (1) | 2 (0) |
| (d) FOURTH CHANNEL CD | 3 (9) | 3 (8) | 3 (7) | 3 (6) | 3 (5) | 3 (4) | 3 (3) | 3 (2) | 3 (1) | 3 (0) |
| (e) FIFTH CHANNEL CE | 4 (9) | 4 (8) | 4 (7) | 4 (6) | 4 (5) | 4 (4) | 4 (3) | 4 (2) | 4 (1) | 4 (0) |
| (f) SIXTH CHANNEL CF | 5 (9) | 5 (8) | 5 (7) | 5 (6) | 5 (5) | 5 (4) | 5 (3) | 5 (2) | 5 (1) | 5 (0) |
| (g) SEVENTH CHANNEL CG | 6 (9) | 6 (8) | 6 (7) | 6 (6) | 6 (5) | 6 (4) | 6 (3) | 6 (2) | 6 (1) | 6 (0) |
| (h) EIGHTH CHANNEL CH | 7 (9) | 7 (8) | 7 (7) | 7 (6) | 7 (5) | 7 (4) | 7 (3) | 7 (2) | 7 (1) | 7 (0) |
| (i) NINTH CHANNEL CI | 8 (9) | 8 (8) | 8 (7) | 8 (6) | 8 (5) | 8 (4) | 8 (3) | 8 (2) | 8 (1) | 8 (0) |
| (j) TENTH CHANNEL CJ | 9 (9) | 9 (8) | 9 (7) | 9 (6) | 9 (5) | 9 (4) | 9 (3) | 9 (2) | 9 (1) | 9 (0) |

FIG. 5

| | (a) FS1 | (b) FS2 | (c) FS3 | (d) FS4 | (e) FS5 | (f) FS6 | (g) FS7 | (h) FS8 | (i) FS9 | (j) FS10 |
|---|---|---|---|---|---|---|---|---|---|---|
| | EAV1 | EAV1 | EAV1 | EAV1 | EAV1 | EAV1 | EAV1 | EAV1 | EAV1 | EAV1 |
| | EAV2 | EAV2 | EAV2 | EAV2 | EAV2 | EAV2 | EAV2 | EAV2 | EAV2 | EAV2 |
| | EAV3 | EAV3 | EAV3 | EAV3 | EAV3 | EAV3 | EAV3 | EAV3 | EAV3 | EAV3 |
| | EAV4 | EAV4 | EAV4 | EAV4 | EAV4 | EAV4 | EAV4 | EAV4 | EAV4 | EAV4 |
| | 4240 | 4241 | 4242 | 4243 | 4244 | 4245 | 4246 | 4247 | 4248 | 4249 |
| | 4230 | 4231 | 4232 | 4233 | 4234 | 4235 | 4236 | 4237 | 4238 | 4239 |
| | 4220 | 4221 | 4222 | 4223 | 4224 | 4225 | 4226 | 4227 | 4228 | 4229 |
| | 4210 | 4211 | 4212 | 4213 | 4214 | 4215 | 4216 | 4217 | 4218 | 4219 |
| | 4200 | 4201 | 4202 | 4203 | 4204 | 4205 | 4206 | 4207 | 4208 | 4209 |
| | 4190 | 4191 | 4192 | 4193 | 4194 | 4195 | 4196 | 4197 | 4198 | 4199 |
| | ⋮ | ⋮ | ⋮ | ⋮ | ⋮ | ⋮ | ⋮ | ⋮ | ⋮ | ⋮ |
| | 160 | 161 | 162 | 163 | 164 | 165 | 166 | 167 | 168 | 169 |
| | 150 | 151 | 152 | 153 | 154 | 155 | 156 | 157 | 158 | 159 |
| | 140 | 141 | 142 | 143 | 144 | 145 | 146 | 147 | 148 | 149 |
| | 130 | 131 | 132 | 133 | 134 | 135 | 136 | 137 | 138 | 139 |
| | 120 | 121 | 122 | 123 | 124 | 125 | 126 | 127 | 128 | 129 |
| | 110 | 111 | 112 | 113 | 114 | 115 | 116 | 117 | 118 | 119 |
| | 100 | 101 | 102 | 103 | 104 | 105 | 106 | 107 | 108 | 109 |
| | 90 | 91 | 92 | 93 | 94 | 95 | 96 | 97 | 98 | 99 |
| | 80 | 81 | 82 | 83 | 84 | 85 | 86 | 87 | 88 | 89 |
| | 70 | 71 | 72 | 73 | 74 | 75 | 76 | 77 | 78 | 79 |
| | 60 | 61 | 62 | 63 | 64 | 65 | 66 | 67 | 68 | 69 |
| | 50 | 51 | 52 | 53 | 54 | 55 | 56 | 57 | 58 | 59 |
| | 40 | 41 | 42 | 43 | 44 | 45 | 46 | 47 | 48 | 49 |
| | 30 | 31 | 32 | 33 | 34 | 35 | 36 | 37 | 38 | 39 |
| | 20 | 21 | 22 | 23 | 24 | 25 | 26 | 27 | 28 | 29 |
| WD | 10 | 11 | 12 | 13 | 14 | 15 | 16 | 17 | 18 | 19 |
| | 0 | 1 | 2 | 3 | 4 | 5 | 6 | 7 | 8 | 9 |
| | SAV1 | SAV1 | SAV1 | SAV1 | SAV1 | SAV1 | SAV1 | SAV1 | SAV1 | SAV1 |
| | SAV2 | SAV2 | SAV2 | SAV2 | SAV2 | SAV2 | SAV2 | SAV2 | SAV2 | SAV2 |
| | SAV3 | SAV3 | SAV3 | SAV3 | SAV3 | SAV3 | SAV3 | SAV3 | SAV3 | SAV3 |
| | SAV4 | SAV4 | SAV4 | SAV4 | SAV4 | SAV4 | SAV4 | SAV4 | SAV4 | SAV4 |

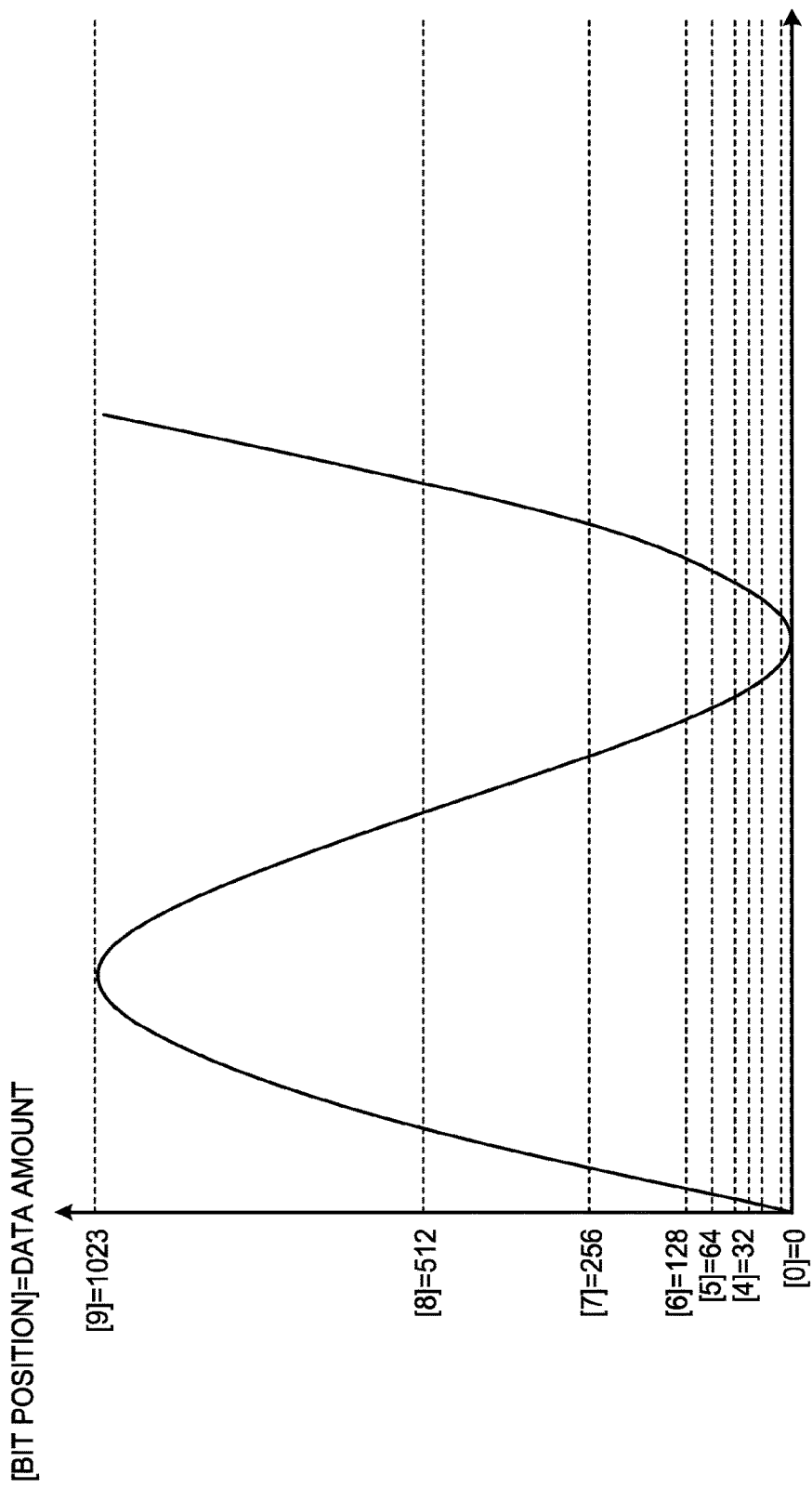

MEDICAL SIGNAL PROCESSING DEVICE AND MEDICAL OBSERVATION SYSTEM

CROSS-REFERENCE TO RELATED APPLICATION(S)

The present application claims priority to and incorporates by reference the entire contents of Japanese Patent Application No. 2016-006644 filed in Japan on Jan. 15, 2016.

BACKGROUND

The present disclosure relates to a medical signal processing device.

Medical observation systems in the medical field are configured to capture an image of the inside of a subject such as a human (inside of a living body) to observe the inside of this living body (for example, refer to Japanese Patent Laid-open No. 2009-61032 and Japanese Patent Laid-open No. 2006-26134).

Medical observation systems disclosed in Japanese Patent Laid-open No. 2009-61032 and Japanese Patent Laid-open No. 2006-26134 ("electronic endoscope systems" in Japanese Patent Laid-open No. 2009-61032 and Japanese Patent Laid-open No. 2006-26134) each include a medical observation device ("electronic endoscope" in Japanese Patent Laid-open No. 2009-61032 and Japanese Patent Laid-open No. 2006-26134) configured to capture an image of the inside of a living body and output an image signal, a control device ("video processor" in Japanese Patent Laid-open No. 2009-61032 and "processor" in Japanese Patent Laid-open No. 2006-26134) configured to receive the image signal from the medical observation device and process the image signal to generate a display image signal, and a signal transmission path ("wireless connector" in Japanese Patent Laid-open No. 2009-61032 and "signal line" in Japanese Patent Laid-open No. 2006-26134) through which the image signal from the medical observation device is transmitted to the control device.

SUMMARY

When a failure occurs in transmission of the image signal due to, for example, breaking of the signal transmission path, the control device is unable to appropriately generate the display image signal and display an image suitable for observation.

In the medical observation system disclosed in Japanese Patent Laid-open No. 2009-61032, when a signal transmission state in the signal transmission path is detected and the detected transmission state is inappropriate for transmission, an operator is warned or notified by, for example, a buzzer. However, in the medical observation system disclosed in Japanese Patent Laid-open No. 2009-61032, an image suitable for observation may not be displayed until the signal transmission path is replaced by, for example, the operator in response to this warning or notification.

The medical observation system disclosed in Japanese Patent Laid-open No. 2006-26134 is provided with at least two signal transmission paths through which an identical image signal is transmitted. With this configuration, in the medical observation system disclosed in Japanese Patent Laid-open No. 2006-26134, when a transmission failure occurs in one of the signal transmission paths, the image signal may be transmitted to the control device through the other signal transmission path, which achieves continuous display of an image suitable for observation. However, one of the signal transmission paths is unnecessary when no transmission failure occurs. In other words, in the medical observation system disclosed in Japanese Patent Laid-open No. 2006-26134, the above-described signal transmission path needs to be redundantly provided, which prevents simplification of the structure.

It has been desired to achieve a technique of performing, with a simplified structure, continuous display of an image suitable for observation when a transmission failure occurs in a signal transmission path.

There is a need for a medical signal processing device and a medical observation system capable of performing, with a simplified structure, continuous display of an image suitable for observation when a transmission failure occurs in a signal transmission path.

A medical signal processing device according to one aspect of the present disclosure receives an image signal in accordance with a result of examining inside of a subject and processes the image signal. The image signal includes a plurality of pixel data groups of respective pixels arrayed at a constant interval among pixels sequentially arrayed in a predetermined direction in an image made of pixels arrayed in a matrix, the pixel data groups are data of respective pixels different from each other, the pixel data groups are received by the medical signal processing device in parallel, the medical signal processing device includes a distribution processing unit configured to generate a plurality of distributed image signals by distributing the pixel data groups, the distribution processing unit distributes the pixel data groups such that, among the pixel data groups, pieces of data at bit positions of most significant digits of the pixel data groups of pixels adjacent to each other are included in the respective distributed image signals different from each other, and the distributed image signals are transmitted to an external medical control device through a plurality of respective signal transmission paths.

BRIEF DESCRIPTION OF THE DRAWINGS

FIG. 3A is a diagram illustrating an image signal output from an imaging unit illustrated in FIG. 2;

FIG. 3B is a diagram illustrating the image signal output from the imaging unit illustrated in FIG. 2;

FIG. 5 is a diagram illustrating first to tenth image signals after S/P conversion processing is executed at an S/P conversion unit illustrated in FIG. 4;

FIG. 9 is a diagram illustrating the effect of the first embodiment of the present disclosure;

DETAILED DESCRIPTION

Figure 1:
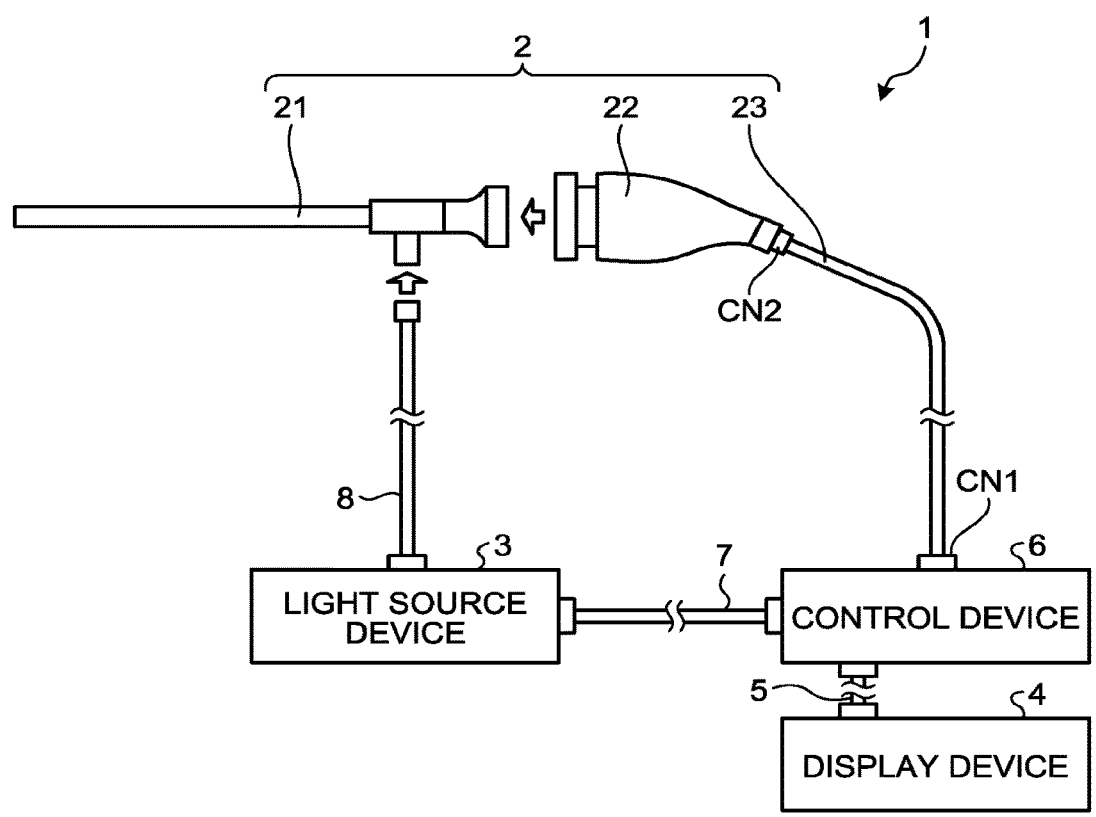
FIG. 1 is a diagram illustrating a schematic configuration of a medical observation system according to a first embodiment of the present disclosure.

Configurations to achieve the present disclosure (hereinafter referred to as embodiments) will be described below with reference to the accompanying drawings. The embodiments described below, however, are not intended to limit the present disclosure. In description of the drawings, any identical parts are denoted by an identical reference numeral.

First Embodiment

Schematic Configuration of Medical Observation System

FIG. 1 is a diagram illustrating a schematic configuration of a medical observation system 1 according to a first embodiment of the present disclosure.

The medical observation system 1 is used in the medical field to observe the inside of a subject such as a human (inside of a living body). As illustrated in FIG. 1, the medical observation system 1 includes an endoscope 2, a light source device 3, a display device 4, a second transmission cable 5, a control device 6, a third transmission cable 7, and a light guide 8.

The endoscope 2 examines the inside of the living body and outputs an image signal (a plurality of transmission image signals) in accordance with a result of this examination. As illustrated in FIG. 1, the endoscope 2 includes an insertion unit 21, a camera head 22, and a first transmission cable 23.

The insertion unit 21 is hard or at least partially soft, has an elongated shape, and is inserted into the inside of the living body. The insertion unit 21 includes an optical system that includes one or a plurality of lenses and through which an object image is condensed.

The light source device 3 is connected with one end of the light guide 8, and supplies, under control of the control device 6, this one end of the light guide 8 with light for illumination of the inside of the living body.

The light guide 8 has one end detachably connected with the light source device 3 and the other end detachably connected with the insertion unit 21. The light guide 8 transfers the light supplied by the light source device 3 from the one end to the other end to supply the light to the insertion unit 21. The light supplied to the insertion unit 21 is emitted from a leading end of the insertion unit 21 and incident on the inside of the living body. The light (object image) incident on the inside of the living body is condensed through the optical system in the insertion unit 21.

The camera head 22 is detachably connected with a base end of the insertion unit 21. The camera head 22 captures, under control of the control device 6, the object image condensed through the insertion unit 21 and generates an image capturing signal (image signal). The camera head 22 also generates a plurality of transmission image signals from this image signal and outputs these transmission image signals. In the first embodiment, the camera head 22 converts these transmission image signals into optical signals and outputs these transmission image signals as the optical signals.

The configuration of the camera head 22 will described later in detail.

The first transmission cable 23 has one end detachably connected with the control device 6 through a connector CN1 (FIG. 1) and the other end connected with the camera head 22 through a connector CN2 (FIG. 1). Specifically, the first transmission cable 23 includes a plurality of electric wires 231 (refer to FIG. 2) and a plurality of optical fibers 232 (refer to FIG. 2) arranged inside of an outer cover, which is an outermost layer.

Figure 2:
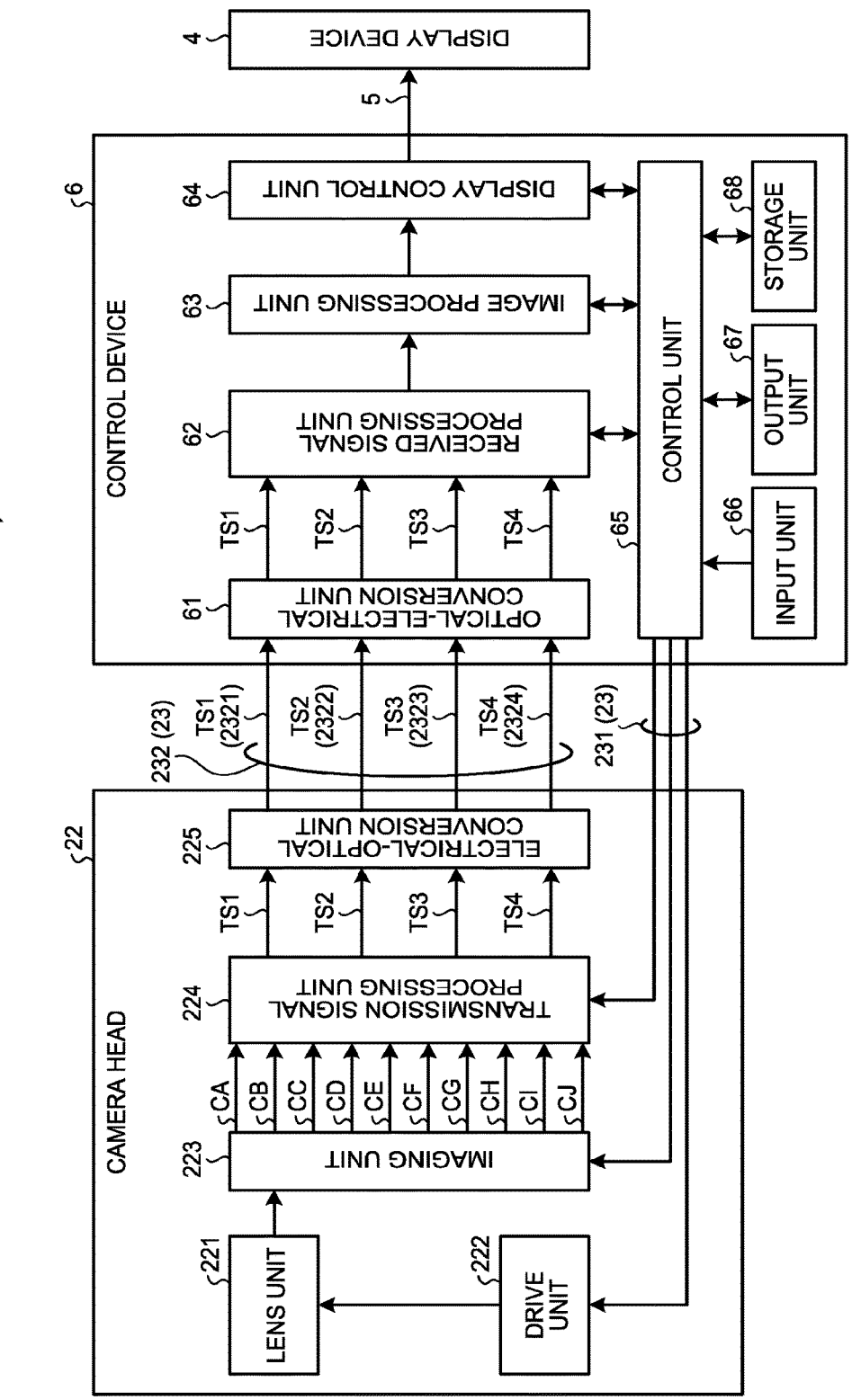
FIG. 2 is a block diagram of the configurations of a camera head and a control device illustrated in FIG. 1.

The electric wires 231 are electric wires for transmitting, for example, a control signal, a synchronizing signal, a clock, and electrical power output from the control device 6 to the camera head 22. In FIG. 2, the number of the electric wires 231 is three but not limited thereto, and may be any other number.

The optical fibers 232 are optical fibers for transmitting, to the control device 6, the transmission image signals (optical signals) output from the camera head 22. In the first embodiment, the four optical fibers 232 of first to fourth optical fibers 2321 to 2324 (refer to FIG. 2) are provided. The number of the provided optical fibers 232 depends on the number of optical signals output from the camera head 22 and is changed in accordance with any change in the number of optical signals.

The optical fibers 232 included in the first transmission cable 23 each function as a signal transmission path according to the present disclosure.

The display device 4 includes a display exploiting, for example, liquid crystal or organic electro luminescence (EL), and displays an image based on image signals processed at the control device 6.

The second transmission cable 5 has one end detachably connected with the display device 4 and the other end detachably connected with the control device 6. The second transmission cable 5 transmits image signals processed at the control device 6 to the display device 4.

The control device 6 includes, for example, a central processing unit (CPU) and performs overall control of operation of the light source device 3, the camera head 22, and the display device 4.

The configuration of the control device 6 will be described later in detail.

The third transmission cable 7 has one end detachably connected with the light source device 3 and the other end detachably connected with the control device 6. The third transmission cable 7 transmits, to the light source device 3, a control signal from the control device 6.

Configuration of Camera Head

The following describes the configuration of the camera head 22.

FIG. 2 is a block diagram of the configurations of the camera head 22 and the control device 6.

For the purpose of description, FIG. 2 omits illustrations of the connectors CN1 and CN2 connecting the control device 6 and the camera head 22 with the first transmission cable 23, and connectors connecting the control device 6 and the display device 4 with the second transmission cable 5.

As illustrated in FIG. 2, the camera head 22 includes a lens unit 221, a drive unit 222, an imaging unit 223, a transmission signal processing unit 224, and an electrical-optical conversion unit 225.

The lens unit 221 includes one or a plurality of lenses movable along an optical axis and images the object image condensed through the insertion unit 21 onto an imaging plane of the imaging unit 223 (an image sensor 2231 (refer to FIG. 3A)). The lens unit 221 is provided with an optical zoom mechanism (not illustrated) that changes an angle of view by moving the one or plurality of lenses, and a focus mechanism (not illustrated) that changes focus.

The drive unit 222 operates, under control of the control device 6, the optical zoom mechanism and the focus mechanism described above to change the angle of view and the focus of the lens unit 221.

The imaging unit 223 images the inside of the living body under control of the control device 6. The imaging unit 223 includes a sensor chip on which, for example, the image sensor 2231 (refer to FIG. 3A), such as a charge-coupled device (CCD) or a complementary metal oxide semiconductor (CMOS), configured to receive the object image condensed through the insertion unit 21 and imaged through the lens unit 221 and convert the object image into an electric signal, and a signal processing unit (not illustrated) configured to perform signal processing (such as A/D conversion) on the electric signal (analog signal) from the image sensor 2231 to output an image signal are integrally formed, and outputs the image signal (digital signal) after the A/D conversion. The signal processing unit (not illustrated) described above does not need to be formed integrally with the image sensor 2231 but may be formed separately.

Further in the first embodiment, the imaging unit 223 outputs the image signal after the A/D conversion through 10 channels (first to tenth channels CA to CJ (FIG. 2)) in parallel. The number of channels is not limited to 10 but may be any other number.

The image signal from the imaging unit 223 according to the first embodiment may be output as differential signals for the respective channels. In this case, for example, the signal processing unit (not illustrated) described above may be provided with a differential conversion unit (not illustrated) configured to convert the image signal after the A/D conversion into differential signals, and the transmission signal processing unit 224 to be described later may be provided with a restoring unit (not illustrated) configured to restore the differential signals to the original image signal.

FIGS. 3A and 3B are each a diagram illustrating the image signal output from the imaging unit 223. Specifically, FIG. 3A is a diagram illustrating a physical arrangement of effective pixels of the image sensor 2231. FIG. 3B is a diagram illustrating the image signal output from the imaging unit 223.

The number of bits per pixel in the image signal output from the imaging unit 223 is 10 in the first embodiment, but may be any other number.

In FIG. 3A, pixels on the first row are denoted by sequential numbers (address numbers of "0", "1", "2", . . . ) starting at the first column. Pixels at the second row are denoted by sequential address numbers (illustrated as, for example, a triangle in FIG. 3A) starting at the first column and following the address number of the pixel at the last column on the first row. The same notation applies to the third row and the following rows. In FIG. 3A, each pixel is denoted by such an address number followed by a reference sign ("CA" to "CJ") in parentheses, of any of the first to tenth channels CA to CJ through which pixel data generated at this pixel is output. In addition, (a) to (j) in FIG. 3B illustrate pixel data (in FIG. 3B, for sake of simplicity, pixel data of pixels at address numbers "0" to "9") output through the first to the tenth channels CA to CJ. In FIG. 3B, an address number indicating a pixel at which pixel data is obtained is provided at each bit position of this pixel data, followed by this bit position (with a most significant bit (MSB; the bit position of a most significant digit) of 9 and a least significant bit (LSB; the bit position of a least significant digit) of "0"in parentheses.

In the first embodiment, as illustrated in FIGS. 3A and 3B, the imaging unit 223 converts pixel data generated at the pixel of address number "0" into serial data, and outputs the serial data bit by bit sequentially from the MSB through the first channel CA. The imaging unit 223 converts pixel data generated at the pixel of address number "1" into serial data, and outputs the serial data bit by bit sequentially from the MSB through the second channel CB. Similarly, the imaging unit 223 converts each piece of pixel data generated at pixels of address numbers "2" to "9" into serial data, and outputs the serial data bit by bit sequentially from the MSB through the third to the tenth channels CC to CJ.

In the pieces of pixel data vertically arranged in FIG. 3B, pieces of data at an identical bit position are output simultaneously through the first to the tenth channels CA to CJ, respectively.

Specifically, the imaging unit 223 outputs, in parallel through the first to the tenth channels CA to CJ as described above, pieces of pixel data (serial data) generated at 10 pixels each in an order of the address number.

In the first embodiment, as illustrated in FIG. 3A, pieces of pixel data generated at pixels at an identical column are output through an identical channel.

Although not illustrated in FIGS. 3A and 3B, the imaging unit 223 outputs timing reference codes "SAV1" to "SAV4" made of four words (one word=10 bits) in parallel through the first to the tenth channels CA to CJ before outputting, in parallel through the first to the tenth channels CA to CJ, pieces of pixel data (serial data) generated at 10 pixels each in an order of the address number (refer to FIG. 5). After outputting, in parallel through the first to the tenth channels CA to CJ, the pieces of pixel data (serial data) generated at 10 pixels each in an order of the address number, the imaging unit 223 outputs timing reference codes "EAV1" to "EAV4" made of four words (one word=10 bits) in parallel through the first to the tenth channels CA to CJ (refer to FIG. 5).

Each image signal output in parallel through the first to the tenth channels CA to CJ described above corresponds to a pixel data group according to the present disclosure.

Figure 4:
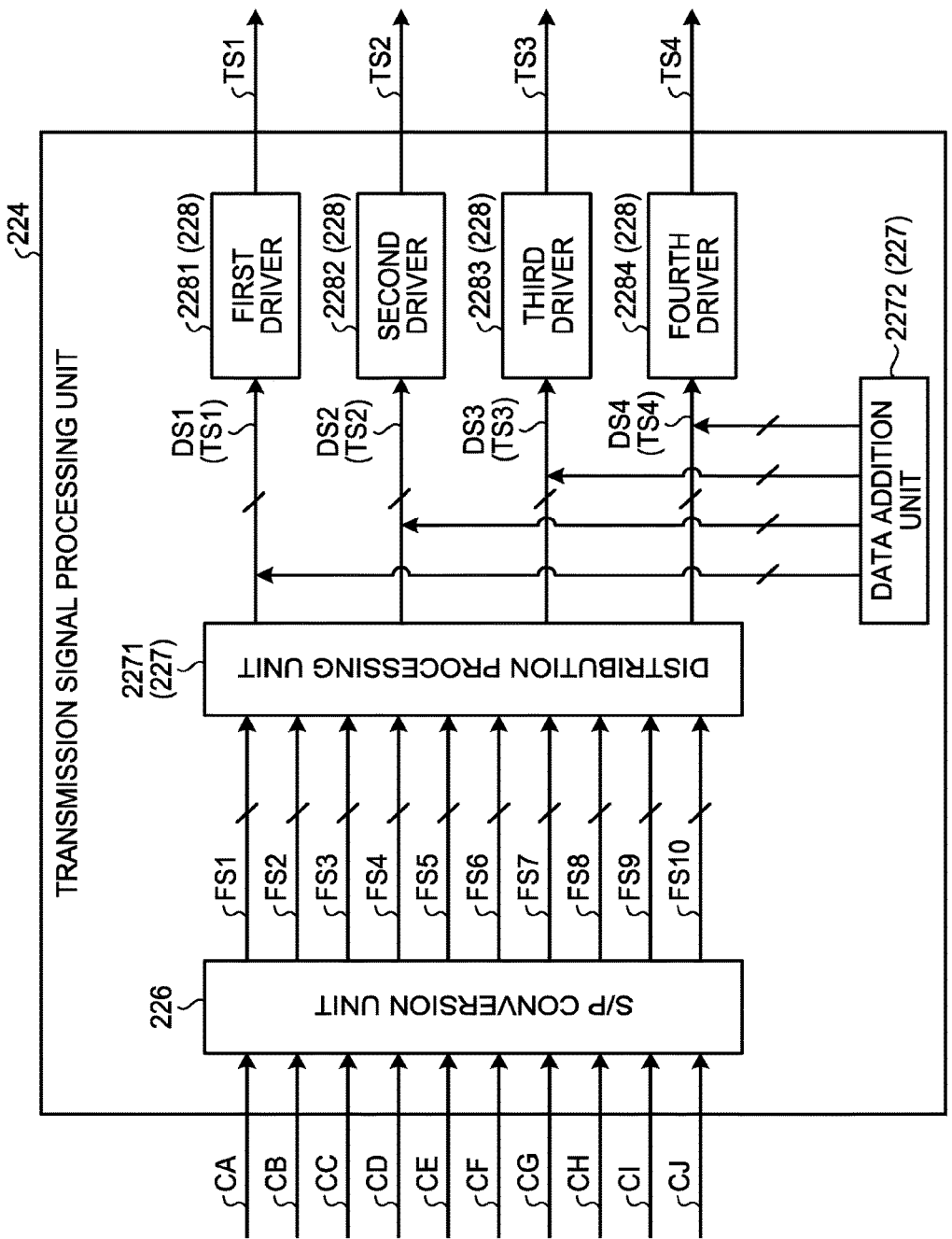
FIG. 4 is a block diagram of the configuration of a transmission signal processing unit illustrated in FIG. 2.

FIG. 4 is a block diagram of the configuration of the transmission signal processing unit 224.

In FIG. 4, the flow of a signal output in parallel data is illustrated by an arrow intersected with a diagonal line. The same notation applies to FIG. 2 and the following figures.

The transmission signal processing unit 224 functions as a medical signal processing device according to the present disclosure and executes, on the image signal (in 10 bits through 10 channels) from the imaging unit 223, various kinds of processing such as S/P conversion processing, transmission image signal generation processing (mapping processing and auxiliary data addition processing), encoding processing (N bit/M (>N) bit conversion processing (in the first embodiment, 8 bits/10 bits conversion processing)), and P/S conversion processing. As illustrated in FIG. 4, the transmission signal processing unit 224 includes an S/P conversion unit 226, a signal processing unit 227, and a plurality of drivers 228.

The S/P conversion unit 226 executes the S/P conversion processing on the image signal (serial data in 10 bits through 10 channels) output from the imaging unit 223 and converts the image signal into parallel data.

FIG. 5 is a diagram illustrating first to tenth image signals FS1 to FS10 (parallel data) after the S/P conversion processing is executed at the S/P conversion unit 226.

Numbers ("0" to "4249") illustrated in FIG. 5 correspond to the address numbers illustrated in FIG. 3A and each indicate pixel data (10 bits) generated at a pixel of the corresponding address number. Pixel data generated at the pixels of address numbers "0" to "4249" is effective data (pixel data obtained in an effective image region).

Specifically, as illustrated in (a) in FIG. 5, the S/P conversion unit 226 generates the first image signal FS1 (parallel data) by executing the S/P conversion processing on an image signal (the timing reference codes "SAV1" to "SAV4" and "EAV1" to "EAV4", and pieces of pixel data (pieces of pixel data generated at the pixels of address numbers "0", "10", "20", . . . )) output through the first channel CA. As illustrated in (b) in FIG. 5, the S/P conversion unit 226 also generates the second image signal FS2 (parallel data) by executing the S/P conversion processing on an image signal (the timing reference codes "SAV1" to "SAV4" and "EAV1" to "EAV4", and pieces of pixel data (pieces of pixel data generated at the pixels of address numbers "1", "11", "21", . . . )) output through the second channel CB. Similarly, as illustrated in (c) to (j) in FIG. 5, the S/P conversion unit 226 generates the third to the tenth image signals FS3 to FS10 (parallel data) by executing the S/P conversion processing on image signals output through the third to the tenth channels CC to CJ.

In the first embodiment, address numbers of "0" to "4249" are provided and thus the number of pixels in the effective image region of the image sensor 2231 is 4250, but the present disclosure is not limited thereto. The number of pixels in the effective image region of an image sensor in use may be changed to any other number as appropriate.

The signal processing unit 227 generates a plurality of transmission image signals by executing the transmission signal generation processing (the mapping processing and the auxiliary data addition processing) on the first to the tenth image signals FS1 to FS10 (parallel data) generated at the S/P conversion unit 226.

In the first embodiment, as illustrated in FIG. 4, the signal processing unit 227 generates four of first to fourth transmission image signals TS1 to TS4 from the first to the tenth image signals FS1 to FS10. The number of transmission image signals is not limited to four but may be any other number.

As illustrated in FIG. 4, the signal processing unit 227 includes a distribution processing unit 2271 and a data addition unit 2272.

The distribution processing unit 2271 generates four of first to fourth distributed image signals DS1 to DS4 by distributing (executing the mapping processing on) the first to the tenth image signals FS1 to FS10 (parallel data) generated at the S/P conversion unit 226.

In the first embodiment, the distribution processing unit 2271 distributes the first to the tenth image signals FS1 to FS10 such that, among the first to the tenth image signals FS1 to FS10, pieces of data of MSBs of the image signals of pixels adjacent to each other are included in respective distributed image signals different from each other among the first to the fourth distributed image signals DS1 to DS4. The distribution processing unit 2271 distributes the first to the tenth image signals FS1 to FS10 such that among the first to the tenth image signals FS1 to FS10, pieces of data at the bit positions of the second MSBs (in the first embodiment, bit position "8") of the image signals of pixels adjacent to each other are included in respective distributed image signals different from each other among the first to the fourth distributed image signals DS1 to DS4. In addition, the distribution processing unit 2271 distributes the first to the tenth image signals FS1 to FS10 such that, among the first to the tenth image signals FS1 to FS10, data of the MSB of one of the image signals of pixels adjacent to each other and data at the bit position of the second MSB of the other image signal are included in respective distributed image signals different from each other among the first to the fourth distributed image signals DS1 to DS4. The distribution processing unit 2271 also distributes the first to the tenth image signals FS1 to FS10 such that data of the MSB of pixel data generated at each pixel and data at the bit position of the second MSB of this pixel data are included in respective distributed image signals different from each other among the first to the fourth distributed image signals DS1 to DS4.

The following describes the first to the fourth distributed image signals DS1 to DS4 generated at the distribution processing unit 2271 with reference to the bit string of word WD illustrated in FIG. 5.

Figure 6:
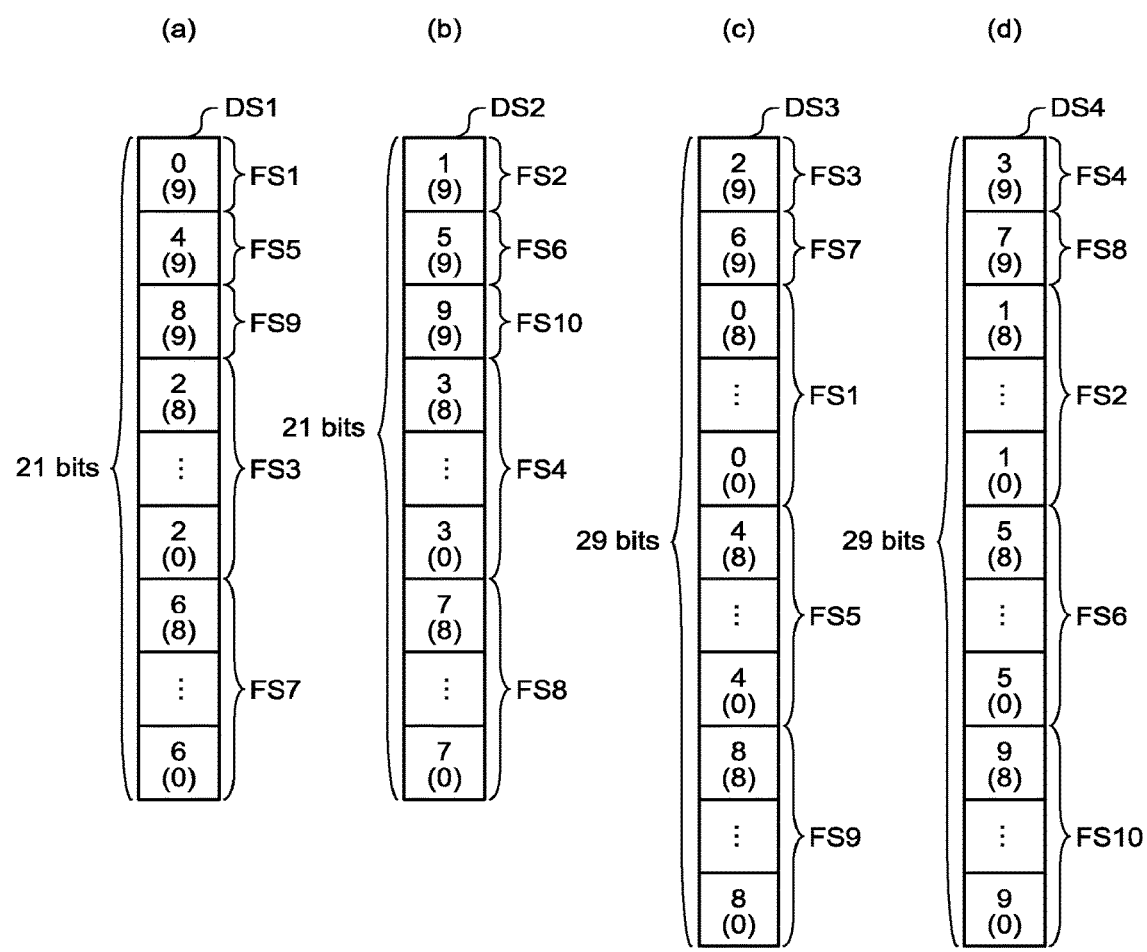
FIG. 6 is a diagram illustrating first to fourth distributed image signals generated at a distribution processing unit illustrated in FIG. 4.

FIG. 6 is a diagram illustrating the first to the fourth distributed image signals DS1 to DS4 generated at the distribution processing unit 2271. Specifically, (a) to (d) in FIG. 6 illustrate distribution of the bit string of word WD illustrated in FIG. 5.

In (a) to (d) in FIG. 6, each bit is denoted by an address number indicating the pixel of the corresponding pixel data, followed by a bit position in this pixel data in parentheses.

Among the first to the tenth image signals FS1 to FS10, image signals of pixels adjacent to each other and image signals of pixels separate from each other exemplarily include image signals described below.

For example, the first image signal FS1 includes pieces of pixel data generated at pixels of address numbers "0", "10", "20", . . . . The second image signal FS2 includes pieces of pixel data generated at pixels of address numbers "1", "11", "21", . . . . Thus, the first and the second image signals FS1 and FS2 are image signals of pixels (address numbers) adjacent to each other. The fifth image signal FS5 includes pieces of pixel data generated at pixels of address numbers "4", "14", "24", . . . . Thus, the first and the fifth image signals FS1 and FS5 are image signals of pixels (address numbers) separate from each other.

Then, as described above, the distribution processing unit 2271 distributes the first to the tenth image signals FS1 to FS10 such that pieces of data of MSBs of the image signals of pixels adjacent to each other are included in distributed image signals different from each other. As a result, as illustrated in (a) in FIG. 6, the first distributed image signal DS1 includes data of the MSB of pixel data generated at the pixel of address number "0" (the first image signal FS1), data of the MSB of pixel data generated at the pixel of address number "4" (the fifth image signal FS5), and data of the MSB of pixel data generated at the pixel of address number "8" (ninth image signal FS9). As illustrated in (b) in FIG. 6, the second distributed image signal DS2 includes data of the MSB of pixel data generated at the pixel of address number "1" (the second image signal FS2), data of the MSB of pixel data generated at the pixel of address number "5" (the sixth image signal FS6), and data of the MSB of pixel data generated at the pixel of address number "9" (the tenth image signal FS10). As illustrated in (c) in FIG. 6, the third distributed image signal DS3 includes data of the MSB of pixel data generated at the pixel of address number "2" (the third image signal FS3), and data of the MSB of pixel data generated at the pixel of address number "6" (the seventh image signal FS7). As illustrated in (d) in FIG. 6, the fourth distributed image signal DS4 includes data of the MSB of pixel data generated at the pixel of address number "3" (the fourth image signal FS4), and data of the MSB of pixel data generated at the pixel of address number "7" (the eighth image signal FS8).

As described above, the distribution processing unit 2271 distributes the first to the tenth image signals FS1 to FS10 such that pieces of data at bit positions "8" of image signals of pixels adjacent to each other are included in distributed image signals different from each other, data of the MSB of one of the image signals of pixels adjacent to each other and data at bit position "8" of the other image signal are included in distributed image signals different from each other, and data of the MSB and data at bit position "8" of pixel data generated at an identical pixel are included in distributed image signals different from each other. As a result, as illustrated in (a) in FIG. 6, the first distributed image signal DS1 includes pieces of data at bit positions "8" of pieces of pixel data (the third and the seventh image signals FS3 and FS7) generated at pixels of address numbers "2" and "6" separate from pixels of address numbers "0", "4", and "8". As illustrated in (b) in FIG. 6, the second distributed image signal DS2 includes pieces of data at bit positions "8" of pieces of pixel data (the fourth and eighth image signals FS4 and FS8) generated at pixels of address numbers "3" and "7" separate from pixels of address numbers "1", "5", and "9". As illustrated in (c) in FIG. 6, the third distributed image signal DS3 includes pieces of data at bit positions "8" of pieces of pixel data (the first, the fifth, and the ninth image signals FS1, FS5, and FS9) generated at pixels of address numbers "0", "4", and "8" separate from pixels of address numbers "2" and "6". As illustrated in (d) in FIG. 6, the fourth distributed image signal DS4 includes pieces of data at bit positions "8" of pieces of pixel data (the second, the sixth, and the tenth image signals FS2, FS6, and FS10) generated at pixels of address numbers "1", "5", and "9" separate from pixels of address numbers "3" and "7".

Pieces of data at bit positions "7" to "0" may be distributed such that the pieces are included randomly in the first to the fourth distributed image signals DS1 to DS4. Alternatively, the pieces may be distributed such that the pieces are included in a distributed image signal including data of bit position "8" of pixel data generated at this pixel as illustrated in FIG. 6.

In the distribution as illustrated in FIG. 6, the first and the second distributed image signals DS1 and DS2 each include 21 bits per word. The third and the fourth distributed image signals DS3 and DS4 each include 29 bits per word.

In FIG. 6, the amount of data (number of bits) per word in the first to the fourth distributed image signals DS1 to DS4 is not constant (21 bits for the first and the second distributed image signals DS1 and DS2, and 29 bits for the third and the fourth distributed image signals DS3 and DS4), but the present disclosure is not limited thereto. The first to the tenth image signals FS1 to FS10 may be distributed so that the amount of data is constant therebetween.

The data addition unit 2272 generates the first to the fourth transmission image signals TS1 to TS4 by adding auxiliary data to (executing the auxiliary data addition processing on) each of the four of the first to the fourth distributed image signals DS1 to DS4 to enable execution of the 8 bits/10 bits conversion processing at a later stage.

In the first embodiment, the data addition unit 2272 adds auxiliary data of 11 bits per word to each of the first and the second distributed image signals DS1 and DS2 (21 bits). The data addition unit 2272 adds auxiliary data of 3 bits per word to each of the third and the fourth distributed image signals DS3 and DS4 (29 bits).

The auxiliary data added to the first to the fourth distributed image signals DS1 to DS4 may be any data that allows execution of the 8 bits/10 bits conversion processing at a later stage.

The drivers 228 are provided in accordance with the number of transmission image signals generated at the signal processing unit 227. Specifically, in the first embodiment, as illustrated in FIG. 4, the four drivers 228 of first to fourth drivers 2281 to 2284 are provided. The four of the first to the fourth drivers 2281 to 2284 execute the encoding processing (in the first embodiment, the 8 bits/10 bits conversion processing) on the first to the fourth transmission image signals TS1 to TS4 generated at the signal processing unit 227. The four of the first to the fourth drivers 2281 to 2284 execute the P/S conversion processing on the first to the fourth transmission image signals TS1 to TS4 after the encoding processing to convert the signals into serial data. Although not specifically illustrated, a clock signal is superimposed on this serial data, and, for example, a K code indicating the start position and the end position of effective data is inserted into the serial data.

The transmission signal processing unit 224 described above is achieved by a programmable logic device such as a field-programmable gate array (FPGA).

The electrical-optical conversion unit 225 converts the first to the fourth transmission image signals TS1 to TS4 (serial data) output from the transmission signal processing unit 224 (the four of the first to the fourth drivers 2281 to 2284) into optical signals, and outputs the optical signals to the first transmission cable 23 (the first to the fourth optical fibers 2321 to 2324). Then, the first to the fourth optical fibers 2321 to 2324 transmit the first to the fourth transmission image signals TS1 to TS4 to the control device 6.

Configuration of Control Device

The following describes the configuration of the control device 6 with reference to FIG. 2.

As illustrated in FIG. 2, the control device 6 includes an optical-electrical conversion unit 61, a received signal processing unit 62, an image processing unit 63, a display control unit 64, a control unit 65, an input unit 66, an output unit 67, and a storage unit 68.

The optical-electrical conversion unit 61 converts the four optical signals (the four of the first to the fourth transmission image signals TS1 to TS4) received through the first to the fourth optical fibers 2321 to 2324 into electric signals (serial data).

Figure 7:
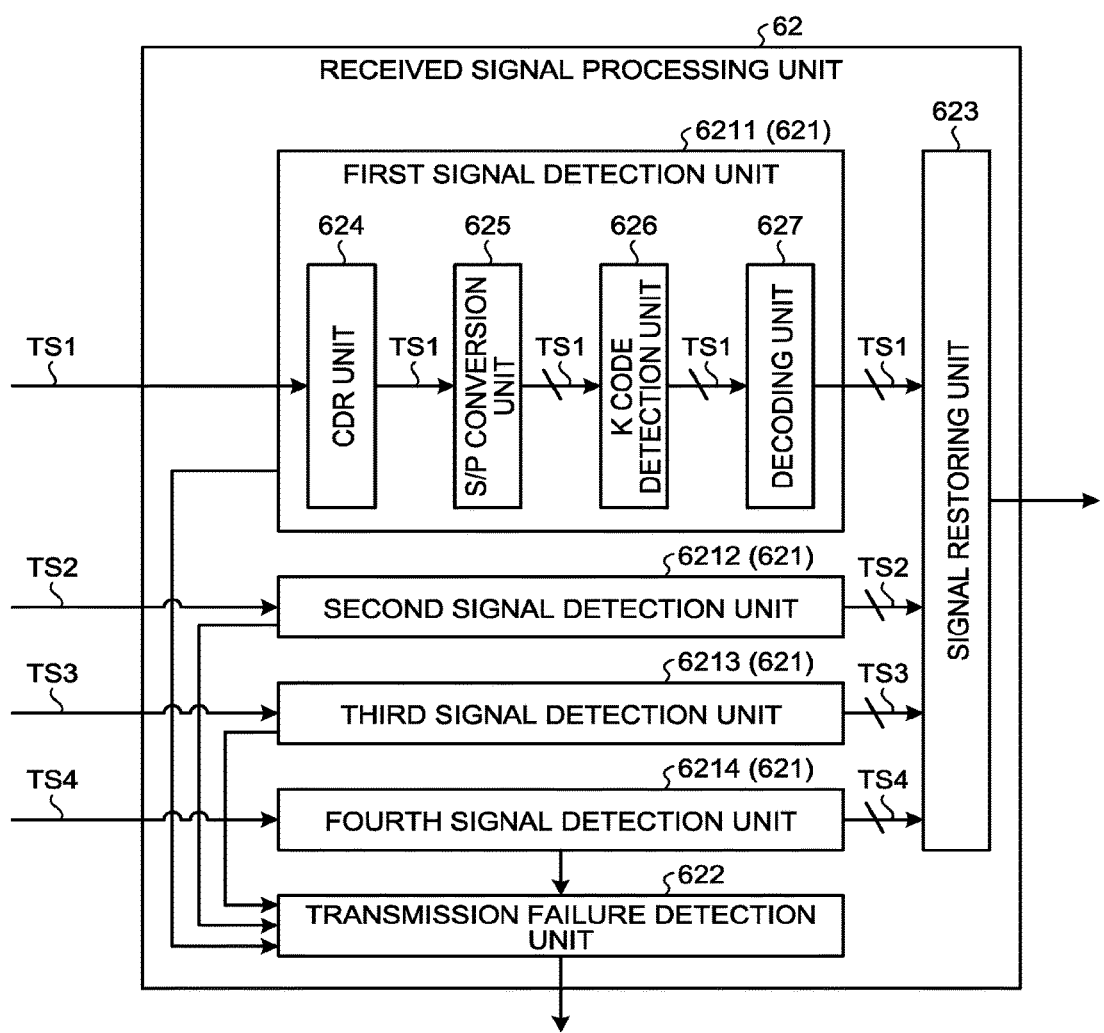
FIG. 7 is a block diagram of the configuration of a received signal processing unit illustrated in FIG. 2.

FIG. 7 is a block diagram of the configuration of the received signal processing unit 62.

The received signal processing unit 62 functions as a medical control device according to the present disclosure and executes, on the four pieces of serial data (the four of the first to the fourth transmission image signals TS1 to TS4) output from the optical-electrical conversion unit 61, various kinds of processing such as transmission failure detection processing, the S/P conversion processing, decoding processing (M bit/N (<M) bit conversion processing (in the first embodiment, 10 bits/8 bits conversion processing)), mapping decoding processing, and the P/S conversion processing. As illustrated in FIG. 7, the received signal processing unit 62 includes a plurality of signal detection units 621, a transmission failure detection unit 622, and a signal restoring unit 623.

The signal detection units 621 are provided in accordance with the number of optical fibers 232 (the first to the fourth transmission image signals TS1 to TS4) included in the first transmission cable 23. Specifically, in the first embodiment, the four signal detection units 621 are provided. Hereinafter, the signal detection units 621 corresponding to the first to the fourth transmission image signals TS1 to TS4 are referred to as first to fourth signal detection units 6211 to 6214, respectively (FIG. 7). The first to the fourth signal detection units 6211 to 6214 have an identical configuration, and thus only the configuration of the first signal detection unit 6211 corresponding to the first transmission image signal TS1 will be described below. For the purpose of description, FIG. 7 only illustrates a specific configuration of the first signal detection unit 6211, whereas specific configurations of the second to the fourth signal detection units 6212 to 6214 are omitted in the illustration.

As illustrated in FIG. 7, the first signal detection unit 6211 includes a clock recovery (CDR) unit 624, an S/P conversion unit 625, a K code detection unit 626, and a decoding unit 627.

The CDR unit 624 executes CDR processing that recovers the superimposed clock signal from the first transmission image signal TS1 (serial data) input to the optical-electrical conversion unit 61 through the optical fiber 232 (first optical fiber 2321) and converted at the optical-electrical conversion unit 61. Then, when the execution of the CDR processing is successful (the recovery of the superimposed clock signal is successful), the CDR unit 624 outputs processing execution information indicating the successful execution to the transmission failure detection unit 622. When the execution of the CDR processing is failed, the CDR unit 624 outputs, to the transmission failure detection unit 622, failed execution information indicating the failure, and identification information for identifying the optical fiber 232 (first optical fiber 2321) corresponding to the CDR unit 624.

The S/P conversion unit 625 executes the S/P conversion processing on the first transmission image signal TS1 (serial data) after the CDR processing to convert the signal into parallel data.

The K code detection unit 626 detects the K code from the first transmission image signal TS1 (parallel data) after the S/P conversion processing at the S/P conversion unit 625 to perform timing detection of data, and executes K code detection processing that acquires the effective data from the first transmission image signal TS1 (parallel data). Then, when the execution of the K code detection processing is successful (the acquisition of the effective data is successful), the K code detection unit 626 outputs processing execution information indicating the successful execution to the transmission failure detection unit 622. When the execution of the K code detection processing is failed, the K code detection unit 626 outputs, to the transmission failure detection unit 622, failed execution information indicating the failure, and identification information for identifying the optical fiber 232 (first optical fiber 2321) corresponding to the K code detection unit 626.

In the first embodiment, the K code detection unit 626 is employed, but the present disclosure is not limited thereto. When information other than the K code is inserted into the first to the fourth transmission image signals TS1 to TS4 by the camera head 22, a component having a function of detecting this information (component that outputs, to the transmission failure detection unit 622, for example, whether this information may be detected) may be employed.

The decoding unit 627 executes the decoding processing (in the first embodiment, 10 bits/8 bits conversion processing) on the first transmission image signal TS1 (effective data (parallel data) acquired at the K code detection unit 626) after the K code detection processing at the K code detection unit 626.

The transmission failure detection unit 622 detects any failure of transmission of optical signals through the first to the fourth optical fibers 2321 to 2324 based on the information output from the first to the fourth signal detection units 6211 to 6214 (the CDR unit 624 and the K code detection unit 626), and specifies an optical fiber in which a transmission failure has occurred.

Specifically, the first to the fourth signal detection units 6211 to 6214 and the transmission failure detection unit 622 execute the transmission failure detection processing to detect any failure of transmission of optical signals through the first to the fourth optical fibers 2321 to 2324, and specifies an optical fiber in which the transmission failure has occurred.

Then, the transmission failure detection unit 622 outputs transmission failure information (information indicating whether a transmission failure has occurred, and when a transmission failure occurs, an optical fiber in which this transmission failure has occurred) to the control unit 65.

The signal restoring unit 623 restores image signals (the first to the tenth image signals FS1 to FS10 (parallel data)) before the mapping processing at the camera head 22 by executing the mapping decoding processing on the first to the fourth transmission image signals TS1 to TS4 (parallel data) after the decoding processing at the decoding units 627 in the first to the fourth signal detection units 6211 to 6214.

Specifically, the signal restoring unit 623 extracts the first to the fourth distributed image signals DS1 to DS4 from the first to the fourth transmission image signals TS1 to TS4 after the decoding processing at the decoding units 627 in the first to the fourth signal detection units 6211 to 6214, respectively. Then, the signal restoring unit 623 restores image signals (the first to the tenth image signals FS1 to FS10) before the mapping processing at the camera head 22 by executing the inverse processing (mapping decoding processing) of the mapping processing at the camera head 22 on these extracted first to fourth distributed image signals DS1 to DS4.

Similarly to the transmission signal processing unit 224, the received signal processing unit 62 described above is achieved by a programmable logic device such as an FPGA.

The image processing unit 63 executes, on an image signal (serial data) restored at the received signal processing unit 62, various kinds of image processing such as development processing (demosaic processing), noise reduction, color correction, color enhancement, and outline enhancement.

The display control unit 64 generates a display image signal from the image signal (serial data) after the various kinds of image processing at the image processing unit 63, and outputs the display image signal to the display device 4 through the second transmission cable 5. Then, the display device 4 displays an image (hereinafter referred to as an observation image) based on this display image signal. When a transmission failure is detected by the transmission failure detection unit 622, the display control unit 64 generates an image signal for displaying, on the display device 4, a superimposed image obtained by superimposing, on the observation image, a message indicating the occurrence of the transmission failure and a message indicating an optical fiber in which the transmission failure has occurred, and outputs the image signal to the display device 4 through the second transmission cable 5. Then, the display device 4 displays the superimposed image (image in which the messages are superimposed on the observation image) based on this image signal.

In other words, the display device 4 functions as a notification unit according to the present disclosure. The display control unit 64 functions as a notification control unit according to the present disclosure.

The control unit 65 includes, for example, a CPU, and controls operation of the light source device 3, the drive unit 222, the imaging unit 223, and the transmission signal processing unit 224, and operation of the entire control device 6 by outputting a control signal through the third transmission cable 7 and the electric wires 231.

The input unit 66 includes, for example, an operation device such as a mouse, a keyboard, or a touch panel to receive an operation by a user.

The output unit 67 includes, for example, a speaker or a printer to output various kinds of information. When a transmission failure is detected by the transmission failure detection unit 622, the output unit 67 outputs sound indicating the occurrence of the transmission failure, and sound indicating an optical fiber in which this transmission failure has occurred.

In other words, the output unit 67 functions as the notification unit according to the present disclosure. The control unit 65 functions as the notification control unit according to the present disclosure.

The notification unit according to the present disclosure is not limited to the display device 4 and the output unit 67, but may be, for example, an LED that gives notification of predetermined information by lighting or flashing.

The medical observation system 1 according to the first embodiment described above achieves an effect described below.

Figure 8A:
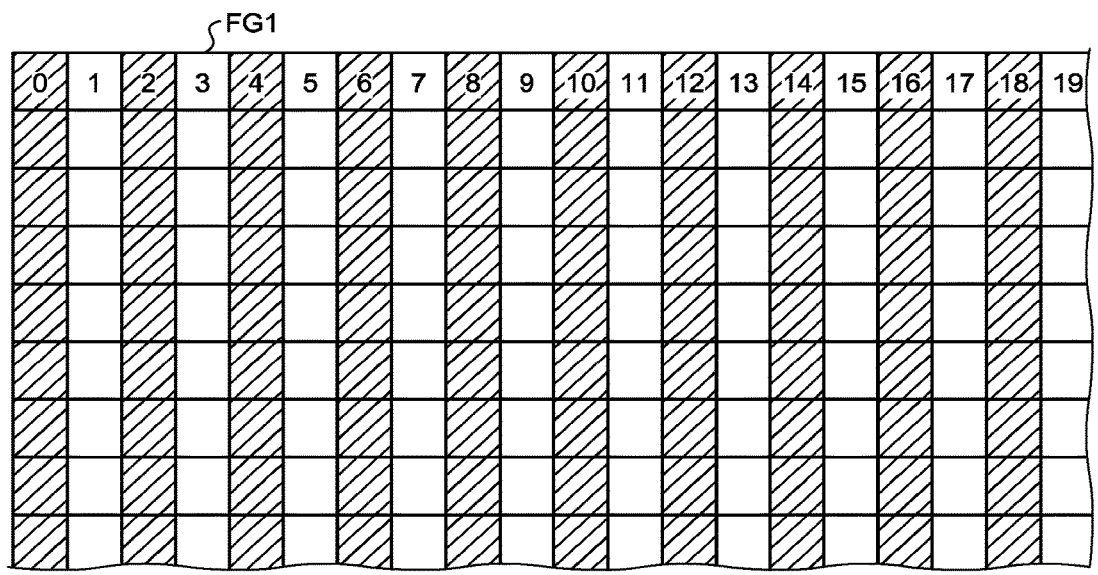
FIG. 8A is a diagram illustrating an effect of the first embodiment of the present disclosure.
Figure 8B:
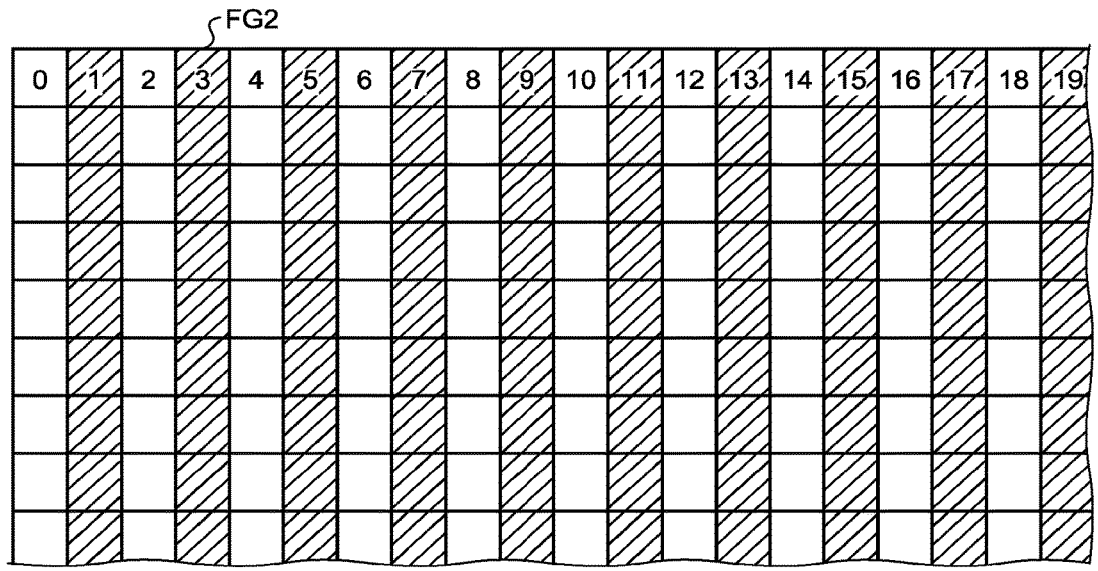
FIG. 8B is a diagram illustrating the effect of the first embodiment of the present disclosure.

FIGS. 8A, 8B, and FIG. 9 are each a diagram illustrating the effect of the first embodiment of the present disclosure. Specifically, FIG. 8A is a diagram illustrating an observation image FG1 displayed on the display device 4 when a transmission failure occurs in any of the first and the third optical fibers 2321 and 2323. FIG. 8B is a diagram illustrating an observation image FG2 displayed on the display device 4 when a transmission failure occurs in any of the second and the fourth optical fibers 2322 and 2324. FIG. 9 is a diagram illustrating the amount of data at each bit position of 10-bit pixel data.

In FIGS. 8A and 8B, for the purpose of illustration, the address number (FIG. 3A) corresponding to each pixel at the image sensor 2231 is attached to part of the observation images FG1 and FG2.

Specifically, in 10-bit pixel data, as illustrated in FIG. 9, the amount of data of the MSB accounts for half of the amount of the entire pixel data. The amount of data at bit position "8" accounts for a quarter of the amount of the entire pixel data. In other words, data at the bit position of a more significant digit is important data in pixel data.

In the medical observation system 1 according to the first embodiment, the first to the tenth image signals FS1 to FS10 are distributed into the first to the fourth distributed image signals DS1 to DS4 such that, among the first to the tenth image signals FS1 to FS10, pieces of data of MSBs of the image signals of pixels adjacent to each other are included in respective distributed image signals different from each other among the first to the fourth distributed image signals DS1 to DS4. In the medical observation system 1, the first to the tenth image signals FS1 to FS10 are distributed into the first to the fourth distributed image signals DS1 to DS4 such that, among the first to the tenth image signals FS1 to FS10, pieces of data at bit positions "8", which are the second MSBs, of the image signals of pixels adjacent to each other are included in respective distributed image signals different from each other among the first to the fourth distributed image signals DS1 to DS4. In the medical observation system 1, the first to the tenth image signals FS1 to FS10 are distributed into the first to the fourth distributed image signals DS1 to DS4 such that, among the first to the tenth image signals FS1 to FS10, data of the MSB of one of the image signals of pixels adjacent to each other and data at bit position "8" of the other image signal are included in respective distributed image signals different from each other among the first to the fourth distributed image signals DS1 to DS4. In the medical observation system 1, the first to the tenth image signals FS1 to FS10 are distributed into the first to the fourth distributed image signals DS1 to DS4 such that data of the MSB of pixel data generated at each pixel and data at bit position "8" of the pixel data are included in respective distributed image signals different from each other among the first to the fourth distributed image signals DS1 to DS4.

As a result, the first distributed image signal DS1 includes data of the MSBs of the first image signal FS1 including pieces of pixel data generated at pixels of address numbers "0", "10", "20", ..., the fifth image signal FS5 including pieces of pixel data generated at pixels of address numbers "4", "14", "24", ..., and the ninth image signal FS9 including pieces of pixel data generated at pixels of address numbers "8", "18", "28", ..., and pieces of data at bit positions "8" of the third image signal FS3 including pieces of pixel data generated at pixels of address numbers "2", "12", "22", ..., and the seventh image signal FS7 including pieces of pixel data generated at pixels of address numbers "6", "16", "26", Thus, when a transmission failure occurs in the first optical fiber 2321, as illustrated in FIG. 8A, in the observation image FG1 displayed on the display device 4, the luminance value is reduced on vertical lines (hatched lines in FIG. 8A) of the first column, the third column, the fifth column, the seventh column, the ninth column, ... corresponding to the first, the third, the fifth, the seventh, and the ninth image signals FS1, FS3, FS4, FS7, and FS9 along with a loss of the first distributed image signal DS1. The same description applies to a case in which a transmission failure has occurred in the third optical fiber 2323 (the third distributed image signal DS3 is lost).

The second distributed image signal DS2 includes data of the MSBs of the second image signal FS2 including pieces of pixel data generated at pixels of address numbers "1", "11", "21", ..., the sixth image signal FS6 including pieces of pixel data generated at pixels of address numbers "5", "15", "25", ..., and the tenth image signal FS10 including pieces of pixel data generated at pixels of address numbers "9", "19", "29", ..., and pieces of data at bit positions "8" of the fourth image signal FS4 including pieces of pixel data generated at pixels of address numbers "3", "13", "23", ..., and the eighth image signal FS8 including pieces of pixel data generated at pixels of address numbers "7", "17", "27", ....

Thus, when a transmission failure occurs in the second optical fiber 2322, as illustrated in FIG. 8B, in the observation image FG2 displayed on the display device 4, the luminance value is reduced on vertical lines (hatched lines in FIG. 8B) of the second column, the fourth column, the sixth column, the eighth column, and the tenth column, ... corresponding to the second, the fourth, the sixth, the eighth, and the tenth image signals FS2, FS4, and FS6, FS8, and FS10 along with a loss of the second distributed image signal DS2. The same description applies to a case in which a transmission failure occurs (the fourth distributed image signal DS4 is lost) in the fourth optical fiber 2324.

In other words, the first to the tenth image signals FS1 to FS10 are distributed such that data of the MSB and data at bit position "8" of pixel data generated at an identical pixel are included in distributed image signals different from each other. With this configuration, when a transmission failure occurs in any of the first to the fourth optical fibers 2321 to 2324 and data of the MSB and bit position "8" of each pixel data included in a distributed image signal corresponding to the optical fiber in which this transmission failure has occurred is lost, the loss may be compensated with data of the other of the MSB and bit position "8" of each pixel data included in a distributed image signal transmitted through an optical fiber in which no transmission failure has occurred. In other words, a transmission failure in any of the first to the fourth optical fibers 2321 to 2324 only causes the reduction in the luminance value but not losses of images at pixels on the hatched vertical lines in FIGS. 8A and 8B.

In addition, the first to the tenth image signals FS1 to FS10 are distributed such that, among the first to the tenth image signals FS1 to FS10, pieces of data of MSBs of the image signals of pixels adjacent to each other are included in distributed image signals different from each other, pieces of data at bit positions "8" of these image signals are included in distributed image signals different from each other, and data of the MSB of one of these image signals and data of bit position "8" of the other image signal are included in distributed image signals different from each other. With this configuration, as illustrated in FIG. 8A or 8B, when a transmission failure occurs in any of the first to the fourth optical fibers 2321 to 2324, any reduction of the luminance value occurs on vertical lines separate from each other, not on vertical lines adjacent to each other. The observation images FG1 and FG2 in which the luminance value is reduced on vertical lines separate from each other allow easier entire recognition thereof than an observation image in which the luminance value is reduced on vertical lines adjacent to each other.

Thus, the observation images FG1 and FG2 suitable for observation may be displayed when a transmission failure occurs in any of the first to the fourth optical fibers 2321 to 2324.

At least two signal transmission paths through which an identical image signal is transmitted are not included in the medical observation system 1 according to the first embodiment, thereby achieving a simplified structure without a redundant signal transmission path that is unnecessary when no transmission failure occurs.

In the medical observation system 1 according to the first embodiment, when a transmission failure is detected, notification of predetermined information (information indicating the occurrence of the transmission failure and an optical fiber in which the transmission failure has occurred) is given through the display device 4 and the output unit 67.

This configuration allows a user such as a doctor to recognize the occurrence of the transmission failure in any of the first to the fourth optical fibers 2321 to 2324. This may also suggest, to this user, replacement of the optical fiber in which the transmission failure has occurred.

In the first embodiment described above, the electrical-optical conversion unit 225 is provided to the camera head 22, but the present disclosure is not limited thereto. For example, the electrical-optical conversion unit 225 may be provided to the first transmission cable 23 including the connector CN2. Moreover, at least part or all of the internal configuration (function) of the transmission signal processing unit 224 as the medical signal processing device according to the present disclosure may be provided to the first transmission cable 23 including the connector CN2. In this case, an electric signal is output from the camera head 22, converted into an optical signal at the electrical-optical conversion unit 225 provided to the first transmission cable 23, and transmitted as a transmission image signal through the optical fibers 232 (signal transmission paths).

Second Embodiment

The following describes a second embodiment of the present disclosure.

In the following description, any component identical to that in the first embodiment described above is denoted by an identical reference sign, and detailed description thereof will be omitted or simplified.

In the medical observation system 1 according to the first embodiment described above, the present disclosure is applied to the endoscope 2 including the camera head 22.

In a medical observation system according to the second embodiment, however, the present disclosure is applied to what is called a video scope including an imaging unit at a leading end of an insertion unit of an endoscope.

Figure 10:
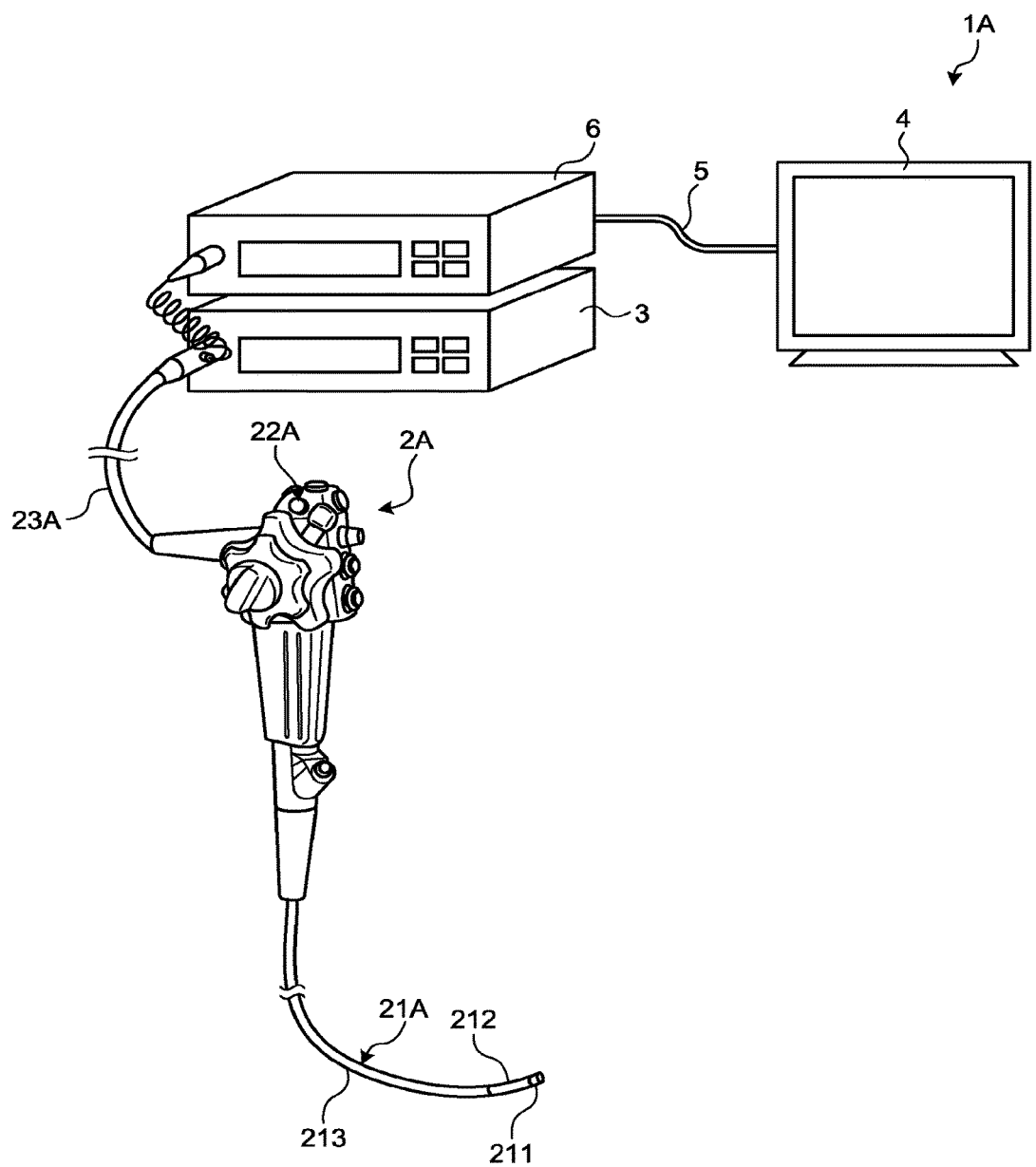
FIG. 10 is a diagram illustrating a schematic configuration of a medical observation system according to a second embodiment of the present disclosure.

FIG. 10 is a diagram illustrating a schematic configuration of a medical observation system 1A according to the second embodiment of the present disclosure.

As illustrated in FIG. 10, the medical observation system 1A according to the second embodiment includes an endoscope 2A configured to generate an image signal by capturing the inside of the body image at an observation site through an insertion unit 21A inserted into the inside of a living body and generate a plurality of transmission image signals from this image signal, the light source device 3 configured to generate illumination light to be emitted from a leading end of the endoscope 2A, the control device 6 configured to receive the transmission image signals generated at the endoscope 2A and process the transmission image signals, and the display device 4 connected with the control device 6 through the second transmission cable 5 and configured to display an image based on the image signals processed at the control device 6.

As illustrated in FIG. 10, the endoscope 2A includes the flexible elongated insertion unit 21A, an operation unit 22A connected with a base end side of the insertion unit 21A and configured to receive inputting of various operation signals, and a universal code 23A extending from the operation unit 22A in a direction different from a direction in which the insertion unit 21A extends and including various built-in cables connected with the light source device 3 and the control device 6.

As illustrated in FIG. 10, the insertion unit 21A includes a leading end part 211 including a built-in imaging unit (not illustrated) configured to generates an image signal by capturing an image of the inside of the living body, a bent part 212 that includes a plurality of bent pieces and may be freely bent, and an elongated flexible tube 213 connected with a base end side of the bent part 212.

Although not illustrated in detail, built-in components similar to the transmission signal processing unit 224 and the electrical-optical conversion unit 225 described in the first embodiment above are included inside the operation unit 22A. The image signal generated at the imaging unit described above is processed at this transmission signal processing unit. The universal code 23A has a configuration substantially same as the first transmission cable 23 described in the first embodiment above. Then, a plurality of transmission image signals (optical signals) processed (generated) inside the operation unit 22A (the transmission signal processing unit and the electrical-optical conversion unit) are output to the control device 6 through the universal code 23A.

When a soft endoscope (the endoscope 2A) is used as in the second embodiment described above, the same effect as that of the first embodiment described above is achieved.

Third Embodiment

The following describes a third embodiment of the present disclosure.

In the following description, any component identical to that in the first embodiment described above is denoted by an identical reference sign, and detailed description thereof will be omitted or simplified.

In the medical observation system 1 according to the first embodiment described above, the present disclosure is applied to the endoscope 2 including the camera head 22.

In a medical observation system according to the third embodiment, however, the present disclosure is applied to a surgical microscope configured to capture an enlarged image of a predetermined viewing region in the inside of a subject (the inside of a living body) or on the surface of the subject (the surface of the living body).

Figure 11:
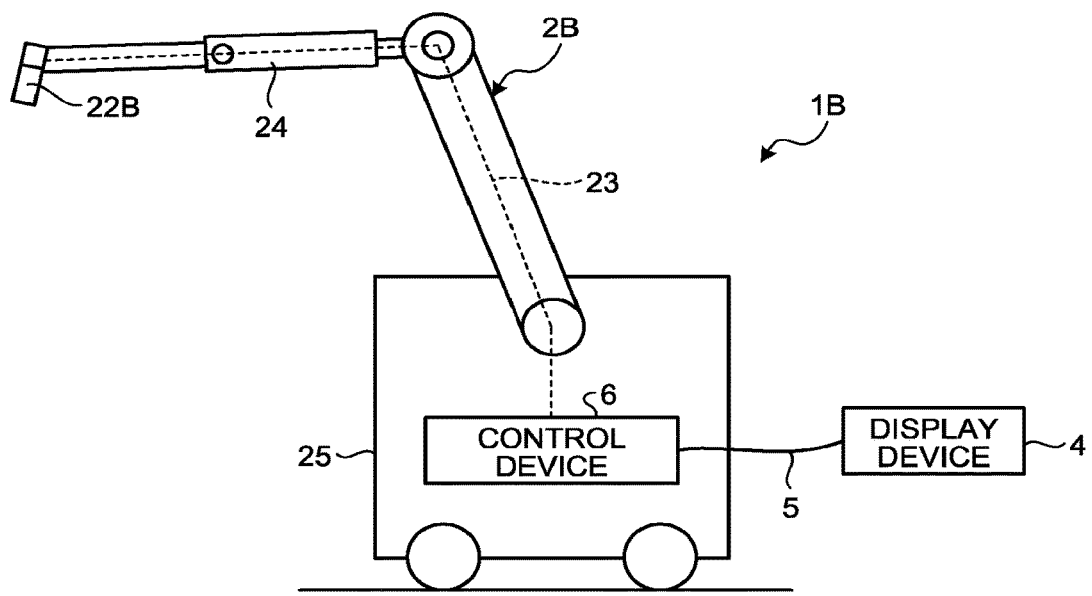
FIG. 11 is a diagram illustrating a schematic configuration of a medical observation system according to a third embodiment of the present disclosure.

FIG. 11 is a diagram illustrating a schematic configuration of a medical observation system 1B according to the third embodiment of the present disclosure.

As illustrated in FIG. 28, the medical observation system 1B according to the sixth embodiment includes a surgical microscope 2B configured to generate an image signal by capturing an image for observing an object and generate a plurality of transmission image signals from this image signal, the control device 6 configured to receive the transmission image signals generated at the surgical microscope 2B and process these transmission image signals, and the display device 4 connected with the control device 6 through the second transmission cable 5 and configured to display an image based on the image signals processed at the control device 6.

As illustrated in FIG. 11, the surgical microscope 2B includes a microscope unit 22B configured to generate an image signal by capturing an enlarged image of a small site of the object and generate a plurality of transmission image signals from this image signal, a support unit 24 connected with a base end part of the microscope unit 22B and including an arm rotatably supporting the microscope unit 22B, and a base unit 25 rotatably holding a base end part of the support unit 24 and movable on a floor surface.

As illustrated in FIG. 11, the control device 6 is installed in the base unit 25.

Instead of being provide movable on the floor surface, the base unit 25 may be fixed on, for example, a ceiling or a wall surface to support the support unit 24. The base unit 25 may include a light source unit configured to generate illumination light to be emitted to the object from the surgical microscope 2B.

Although not illustrated in detail specific, the microscope unit 22B includes an imaging unit configured to generate an image signal by capturing an image of the inside of the living body, and built-in components similar to the transmission signal processing unit 224 and the electrical-optical conversion unit 225 described in the first embodiment above. The image signal generated at the imaging unit is processed at the transmission signal processing unit. Then, a plurality of transmission image signals (optical signals) processed (generated) at the microscope unit 22B (the transmission signal processing unit and the electrical-optical conversion unit) are output to the control device 6 through the first transmission cable 23 wired along the support unit 24.

When the surgical microscope 2B is used as in the third embodiment described above, the same effect as that of the first embodiment described above is achieved.

Other Embodiments

The configurations to achieve the present disclosure are described above, but the present disclosure is not limited to the first to the third embodiments described above.

In the first to the third embodiments described above, a plurality of transmission image signals are transmitted as optical signals from the camera head 22, the operation unit 22A, and the microscope unit 22A to the control device 6, but the present disclosure is not limited thereto. The transmission image signals may be transmitted as electric signals. In other words, the optical fibers 232 as signal transmission paths according to the present disclosure included in the first transmission cable 23 and the universal code 23A may be replaced with electric wires. In this case, the electrical-optical conversion unit 225 and the optical-electrical conversion unit 61 are omitted.

In the transmission signal processing unit 224 according to the first to the third embodiments described above, the auxiliary data addition processing is executed after the mapping processing, but the present disclosure is not limited thereto. The mapping processing may be executed after the auxiliary data addition processing (in which auxiliary data is added to the first to the tenth image signals FS1 to FS10, and the first to the fourth transmission image signals TS1 to TS4 are generated by distributing the first to the tenth image signals FS1 to FS10 to which this auxiliary data is added).

In the first to the third embodiments described above, the scheme of distribution of the first to the tenth image signals FS1 to FS10 to generate the first to the fourth distributed image signals DS1 to DS4 is not limited to the distribution schemes described in the first to the third embodiments above. Any other distribution scheme may be employed as long as, among the first to the tenth image signals FS1 to FS10, pieces of data of MSBs of the image signals of pixels adjacent to each other are included in distributed image signals different from each other through the scheme.

A medical signal processing device according to the present disclosure generates a plurality of distributed image signals by distributing a plurality of pixel data groups received by the medical signal processing device in parallel such that, among the pixel data groups, pieces of data at the bit positions of the most significant digits of the pixel data groups of pixels adjacent to each other are included in the respective distributed image signals different from each other. Then, the distributed image signals are transmitted to an external medical control device through a plurality of respective signal transmission paths.

A transmission failure that has occurred in any of the signal transmission paths results in a loss of a distributed image signal corresponding to the signal transmission path in which this transmission failure has occurred. The distributed image signals generated at the medical signal processing device according to the present disclosure include one of pieces of data at the bit positions of the most significant digits of the pixel data groups of pixels adjacent to each other, but do not include the other piece of data. In pixel data, the amount of data at the bit position of the most significant digit is larger than the amount of data at any other bit position, and thus the data at the bit position of the most significant digit is extremely important.

With this configuration, unlike a configuration in which a plurality of distributed image signals are generated by distributing a plurality of pixel data groups such that pieces of data at the bit positions of the most significant digits of the pixel data groups of pixels adjacent to each other are included in an identical distributed image signal, any loss of data at the bit position of the most significant digit occurs at pixels separate from each other, not at pixels adjacent to each other, when a transmission failure occurs in any of the signal transmission paths. An image in which a loss of data at the bit position of the most significant digit occurs at pixels separate from each other allows easier entire recognition thereof than an image in which a loss of data at the bit position of the most significant digit occurs at pixels adjacent to each other.

With this configuration, an image suitable for observation may be continuously displayed when a transmission failure occurs in a signal transmission path. In addition, a simplified structure without a redundant signal transmission path that is unnecessary when no transmission failure occurs may be achieved because the distributed image signals different from each other are transmitted to the external medical control device through the respective signal transmission paths.

A medical observation system according to the present disclosure includes the medical signal processing device and the medical control device described above, and thus provides an effect similar to the above-described effect of the medical signal processing device.

It should be understood by those skilled in the art that various modifications, combinations, sub-combinations and alterations may occur depending on design requirements and other factors insofar as they are within the scope of the appended claims or the equivalents thereof.

What is claimed is:

1. A medical signal processing device, comprising:
processing circuitry including hardware and configured to
receive an image signal, wherein the image signal includes a plurality of pixel data groups of respective pixels arrayed at a constant interval among pixels sequentially arrayed in a predetermined direction in an image made of pixels arrayed in a matrix, wherein the pixel data groups are data of respective pixels different from each other, and wherein the pixel data groups are received in parallel,
generate a plurality of distributed image signals by distributing the pixel data groups,
distribute the pixel data groups such that, among the pixel data groups, pieces of data at bit positions of most significant digits of the pixel data groups of pixels adjacent to each other are included in the respective distributed image signals different from each other, and
control transmission of the distributed image signals to an external medical control device through a plurality of respective signal transmission paths.

2. The medical signal processing device according to claim 1, wherein the processing circuitry is further configured to distribute the pixel data groups such that, among the pixel data groups, pieces of data at bit positions of second most significant digits of the pixel data groups of pixels adjacent to each other are included in the respective distributed image signals different from each other.

3. The medical signal processing device according to claim 1, wherein the processing circuitry is further configured to distribute the pixel data groups such that, among the pixel data groups, data at a bit position of a most significant digit of one of the pixel data groups of pixels adjacent to each other and data at a bit position of a second most significant digit of the other pixel data group are included in the respective distributed image signals different from each other.

4. The medical signal processing device according to claim 1, wherein the processing circuitry is further configured to distribute the pixel data groups such that data at a bit position of a most significant digit of pixel data of each pixel and data at a bit position of a second most significant digit of the pixel data are included in the distributed image signals different from each other.

5. A medical observation system comprising:
a medical signal processing device including processing circuitry including hardware and configured to receive an image signal, wherein the image signal includes a plurality of pixel data groups of respective pixels arrayed at a constant interval among pixels sequentially arrayed in a predetermined direction in an image made of pixels arrayed in a matrix, wherein the pixel data groups are data of respective pixels different from each other, and wherein the pixel data groups are received in parallel, to generate a plurality of distributed image signals by distributing the pixel data groups, to distribute the pixel data groups such that, among the pixel data groups, pieces of data at bit positions of most significant digits of the pixel data groups of pixels adjacent to each other are included in the respective distributed image signals different from each other, and control transmission of the distributed image signals to an external medical control device through a plurality of respective signal transmission paths;
a plurality of signal transmission paths through which the respective distributed image signals transmitted from the medical signal processing device are transmitted; and
a medical control device including second processing circuitry including hardware and configured to receive the distributed image signals through the signal transmission paths and restore the image signal based on the distributed image signals.

6. The medical observation system according to claim 5, wherein the second processing circuitry is further configured to
detect a signal transmission failure in the signal transmission paths,
give notification of predetermined information, and
give notification of the predetermined information when a transmission failure is detected.

7. The medical observation system according to claim 5, wherein
the signal transmission paths each include a light transmission path through which an optical signal is transmitted, and
the medical observation system includes:
an electrical-optical conversion circuitry configured to convert a plurality of electric signals based on the distributed image signals into a plurality of respective optical signals, and output the optical signals to the respective signal transmission paths, and
an optical-electrical conversion circuitry configured to convert the optical signals received through the signal transmission paths into a plurality of respective electric signals, and output the electric signals to the medical control device.

* * * * *